(12) United States Patent
Sutherland

(10) Patent No.: US 6,890,565 B2
(45) Date of Patent: May 10, 2005

(54) PROCESS FOR PREPARING COAGULANTS FOR WATER TREATMENT

(75) Inventor: John Paul Sutherland, Leicester (GB)

(73) Assignee: Optima Environnment S.A. (CH)

( * ) Notice: Subject to any disclaimer, the term of this patent is extended or adjusted under 35 U.S.C. 154(b) by 0 days.

(21) Appl. No.: 10/149,385

(22) PCT Filed: Apr. 2, 2001

(86) PCT No.: PCT/GB01/01494
§ 371 (c)(1),
(2), (4) Date: Jun. 12, 2002

(87) PCT Pub. No.: WO01/74843
PCT Pub. Date: Oct. 11, 2001

(65) Prior Publication Data
US 2002/0192315 A1 Dec. 19, 2002

(30) Foreign Application Priority Data
Mar. 31, 2000 (GB) ............................................. 0007829

(51) Int. Cl.[7] ............................................. A61K 35/78
(52) U.S. Cl. ............................ 424/725; 424/776; 514/2
(58) Field of Search ............................. 424/195.1, 725, 424/776; 514/2

(56) References Cited
FOREIGN PATENT DOCUMENTS
WO   WO 00/46243   8/2000

OTHER PUBLICATIONS

Okuda et al, "Improvement of Extraction Method of Coagulation Active Components from Moringa Oleifera Seed", Water Research, NL, Elsevier Science Publishers, Amsterdam, vol. 33, No. 15, Oct. 1999, pp. 3373–3378.

Ndabigengesere et al, Active Agents and Mechanism of Coagulation of Turbid Waters Using *Moringa Oleifera*, Water Research, NL, Elsevier Science Publishers, Amsterdam, vol. 29, No. 2, Feb. 1, 1995.

Primary Examiner—Patricia Leith
(74) Attorney, Agent, or Firm—Nixon & Vanderhye, P.C.

(57) ABSTRACT

The invention relates to a process for preparing proteins that can act as effective coagulants in the treatment and purification of contaminated water. In particular, the invention relates to a process for extracting coagulant protein derivatives from the seeds of trees from the family Moringaceae. The invention also relates to coagulation protein preparations prepared by the process, and the use of such preparations for the treatment and purification of contaminated water.

12 Claims, 2 Drawing Sheets

PROCESS FOR PREPARING COAGULANTS FOR WATER TREATMENT

This application is the US national phase of international application PCT/GB01/01494 filed Apr. 2, 2001 which designated the U.S.

The present invention relates to a process for preparing proteins that can act as effective primary coagulants in the treatment and purification of contaminated water. In particular it relates to a process for extracting coagulant protein derivatives from seeds of trees within the family Moringaceae and especially those of *Moringa oleifera* Lam (syns *Moringa pterygosperma* Gaertn.).

The seeds of *Moringa oleifera* Lam (hereinafter referred to as *Moringa*) are utilised primarily to obtain an edible oil, which is extracted using a mechanical press. The residue from this extraction process is known as presscake. It has been found that the seeds of *Moringa oleifera* contain water soluble, low molecular weight, highly basic proteins that can act as primary coagulants in contaminated water treatment. The crushed/powdered seed suspensions and presscake, which remains following oil extraction, have been found to be effective coagulants but they suffer from the disadvantage that they result in a large amount of residual insoluble material which requires disposing of.

The object of the present invention is to provide an extraction process which results in the maximum yield of coagulation proteins from *Moringa* seeds. The extraction process should preferably be suitable for use in less developed countries thereby providing inexpensive coagulant proteins for water treatment.

According to one aspect of the invention there is provided a process for preparing coagulation proteins from *Moringa* seeds which comprises the steps of:
1. treating *Moringa* seed presscake and/or whole seed inclusive of shell to produce an evenly divided granular powder having for example a particle size of from 0.5 to 2.5 mm diameter; and
2. adding the granular powder to a complex salt solution, preferably an aqueous solution containing chlorides of calcium (typically 0.5–1.5 g/l), magnesium (typically 3.0–5.0 g/l), potassium (typically 0.5–1.0 g/l) and sodium (typically 20–30 g/l), in order to leach protein out of the powder; and
3. separating the protein solution from the remaining solids; and
4. precipitating certain organic compounds including proteins, enzymes and carbohydrates, by heating the solution; and
5. removing the precipitates from solution and removing excess water to concentrate the product protein preferably in the form of a suspension of solids.

The process preferably comprises the additional step of drying the protein slurry to a moisture content of 15% or less, preferably 10% or less, most preferably 5% or less.

The extraction process is a series of unit operations, each set up to perform an essential step in the extraction of proteins and their conversion into a state for practical use from the seeds of the *Moringa oleifera* Lam tree.

The process will be further described with reference to the accompanying figures in which.

Figure 1:
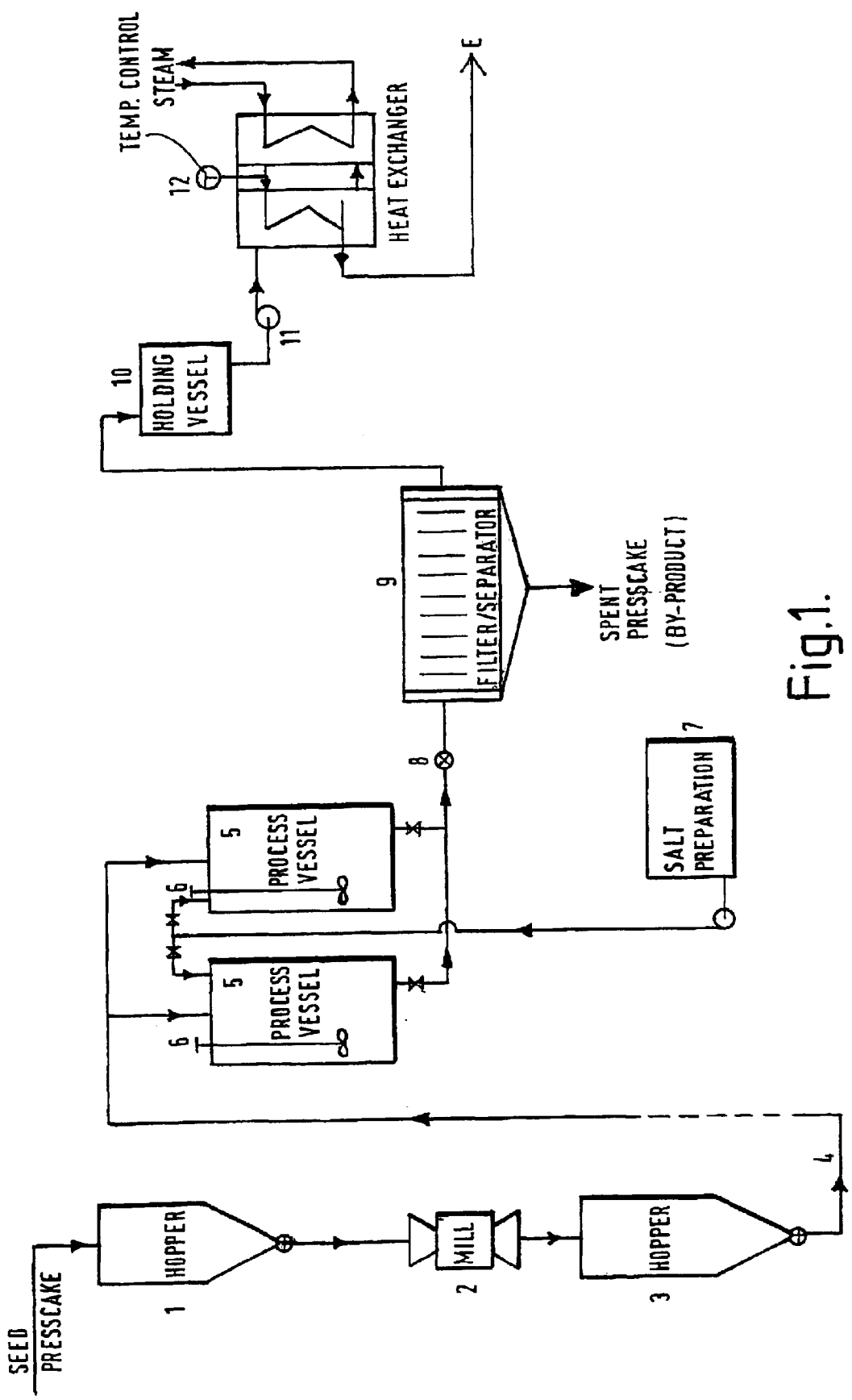
FIG. 1 is a schematic drawing of the first part of the process.
Figure 2:
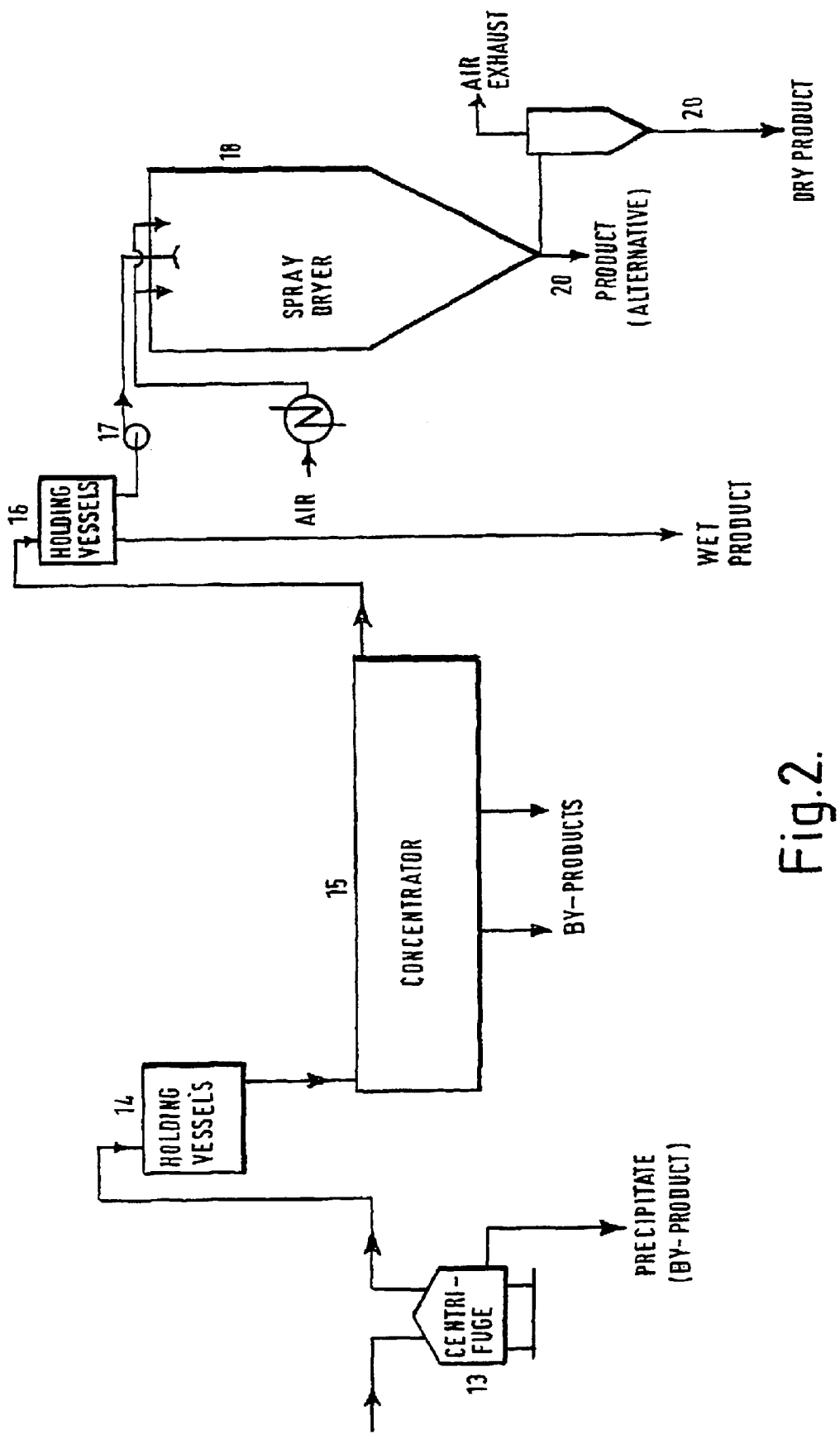
FIG. 2 is a schematic drawing of the second part of the process.

The unit operations of the process are taken in sequence.

Size Reduction

The presscake is received as an unevenly sized, randomly agglomerated granular material.

This operation consists of a feed hopper (1) from which the presscake is fed at a controlled rate into a mill (2) the design principles of which are suitable for the presscake.

On leaving the mill the presscake has been converted to an evenly divided granular powder of a particle size typically 0.5–2.5 mm diameter, preferably 1–2 mm diameter, and with a minimum of very fine particles which would reduce the efficiency of a later separation operation.

The milled product is collected in a receiving hopper (3) incorporating an exhaust duct for the airflow induced by the mill. The receiving hopper has a device such as a rotary valve to facilitate discharge of the product into containers or onto a conveyor (4) for transport to the extraction operations.

Extraction

This consists of one or more process vessels (5) and a facility (7) for providing a complex salt solution, i.e. typically an aqueous solution containing chlorides of calcium (1 g/l), magnesium (4 g/l), potassium (0.75 g/l) and sodium (24 g/l).

The process vessel is typically a vertical cylindrical tank with a base sloping to a discharge outlet and equipped with a mixer (6) employing a propeller or dispersion type rotating agitator.

In operation, the vessel is filled with the complex salt solution and the granular powder is added in a specified proportion, typically 20% w/w and thoroughly dispersed.

It is then continuously agitated under ambient temperature conditions for a period of time sufficient for the complex salt solution to leach the protein out of the dispersed powder. Whilst the period of time may be varied to suit the nature of the powder, approximately 1 hour has been found effective.

At the completion of the leaching operation, the contents of the vessel are in the form of a slurry with spent presscake solids suspended in the solution of complex salt and extracts.

The slurry is transferred using a positive displacement pump (8) to a decanting centrifuge or a filter press, and most effectively the latter, to separate the solution from the spent powder solids. The spent powder has a moisture content in the range of, for example, 15–30%. The recovered solution is collected in holding vessels (10).

Separation of Proteins

From holding vessels (10) the solution of complex salt and extracts is transferred by pump (11) to a system of heat exchangers (12) in which its temperature is raised above 70° C. and typically to 95° C. for a period of between 0.5 and 1 minute. Sufficient agitation, either through hydraulic or mechanical means, is provided to ensure precipitated material does not get burnt onto the container surface. The main section of the heat exchangers may use steam as an indirect heating medium with a suitable temperature control system for the solution. Optimum energy efficiency is achieved in the primary section of the heat exchangers by using the outgoing hot solution to indirectly heat the ingoing cold solution.

During the operation of raising the temperature of the solution above 70° C. certain organic compounds (including proteins, enzymes and carbohydrates) are precipitated to form a solid suspension in the solution. These materials are a by-product and the suspension is discharged from the heat exchangers through a separator (13), typically a centrifuge used for continuous operation of disk-stack design. The precipitated materials are collected as a dense slurry or cake and the clarified solution is discharged directly from the centrifuge under pressure to holding vessels (14).

Concentration

From holding vessels (14) the solution is fed to an operation in which excess water is removed. This may take the form of a multistage vacuum evaporator or preferably a selective membrane filter commonly known as an ultrafilter (15). The latter method is used when considered desirable to remove low molecular weight solutes from the solution in addition to water and is undertaken using a membrane typically of nominal pore size 5,000 Kilo Daltons and a differential pressure typically of 20 psi. The whole operation typically makes a 10 fold increase in the concentration of the product protein. The concentrated product is discharged in the form of a suspension of solids in a saturated solution which is transferred into holding vessels (16).

The concentrated product held in vessels (16) may be packed and distributed for direct use (as a flocculating agent). Alternatively, it may be dehydrated in a drying operation fed by a pump (17) from the vessels (16).

Drying

If the process is conveniently located, the protein in the state of a thick slurry is available for immediate use (as a water treatment aid). However, it must be assumed that in the form of a large scale efficient factory it will be remote from the various points of use of the protein. For this major purpose, the state of the protein is changed to that of a dry powder in which it is resistant to degradation and is convenient for storage, transport and use.

This operation includes a system for drying the thick slurry to a moisture content preferably 15% or less and producing the protein in a finely divided form for convenience of use.

Freeze drying is a method which dries the protein to a friable solid which breaks up to a fine granular state. The preferred method is spray-drying which dries the protein without unwanted degradation and simultaneously converts it to a fine powder.

The spray dryer (18) consists of a chamber into which the slurry is fed at a controlled rate by a positive displacement variable capacity pump (17). The slurry is dispersed in the chamber in the form of very small droplets by means of an atomiser nozzle or atomiser rotating disk. A large volume of air is simultaneously introduced which has been heated to a temperature typically of 200° C. The method achieves a rapid rate of evaporation of the water component of the slurry without raising the product temperature to a damaging level and for this protein the discharge temperature is limited to 100° C. or less, preferably a range of 80°–90°, most preferably a range of 84–87° C.

The final product is discharged at two available locations (20) from the spray drying system via a rotary valve or similar method from which it is filled directly into containers for transport or into a conveyor system for transfer to a filling process.

In use, the liquid concentrate is typically diluted 2:1 in clean water and an applied at doses of 1–20 mg/l (equivalent protein content) for portable water treatment depending on the nature of the water to be treated. For wastewater applications the dose range will be between 5 and 50 mg/l (equivalent protein content).

The dry product is prepared as a 5% (w/v) stock solution in clean water and dosed at similar amounts, based on equivalent protein content, as the liquid concentrate depending on application.

What is claimed is:

1. A process for preparing coagulant proteins from seeds of trees of the family Moringaceae which process comprises the steps of:

a) treating seed presscake and/or whole seed to produce an evenly divided granular powder;

b) adding the granular powder to a salt solution comprising chlorides of calcium, magnesium, potassium and sodium to extract protein, in a solution, out of the powder, c) separating the protein solution from any remaining solids;

d) precipitating certain organic compounds by heating the solution, wherein said heating comprises raising the temperature above 70° C., and wherein said certain organic compounds comprise proteins, enzymes and carbohydrates; and e) removing the precipitates from solution and removing excess water to yield and concentrate said coagulant proteins.

2. A process according to claim 1, wherein said coagulant proteins are a protein slurry, and which comprises an additional step of drying the protein slurry to a moisture content of 15% or less.

3. A process according to claim 1, wherein the seeds are derived from *Moringa oleifera* Lam.

4. A process according to claim 1, wherein the granular powder has a particle size from 0.5 to 2.5 mm diameter.

5. A process according to claim 4, wherein the granular powder has a particle size of from 1 to 2 mm diameter.

6. A process according to claim 1, wherein the salt solution comprises an aqueous solution containing chlorides of calcium (0.5–1.5 g/l), magnesium (3.0–5.0 g/l), potassium (0.5–1.0 g/l) and sodium (20–30 g/l).

7. A process according to claim 1, wherein the protein solution and precipitated materials are separated by centrifuging.

8. A process according to claim 1, wherein the protein solution is concentrated by filtration.

9. A process according to claim 1, wherein the protein solution is spray dried.

10. A process according to claim 1, wherein the protein solution is freeze dried.

11. A coagulation protein preparation suitable for use in the purification of water when prepared according to claim 1.

12. A method of treating or purifying contaminated water comprising:

a) obtaining water to be treated or purified, and b) applying to the water a coagulant protein preparation according to claim 11.

* * * * *